US011579106B2

(12) United States Patent
Chandak et al.

(10) Patent No.: US 11,579,106 B2
(45) Date of Patent: Feb. 14, 2023

(54) HIGH ACCURACY IMPEDANCE MEASUREMENT

(71) Applicant: Texas Instruments Incorporated, Dallas, TX (US)

(72) Inventors: Aatish Chandak, Bengaluru (IN); Raja Reddy Patukuri, Bengaluru (IN); Aravind Miriyala, Bengaluru (IN); Sandeep Oswal, Bengaluru (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 295 days.

(21) Appl. No.: 16/852,736

(22) Filed: Apr. 20, 2020

(65) Prior Publication Data

US 2021/0003523 A1 Jan. 7, 2021

(30) Foreign Application Priority Data

Jul. 1, 2019 (IN) .............................. 201941026256

(51) Int. Cl.
*G01N 27/02* (2006.01)
*A61B 5/053* (2021.01)
*A61B 5/00* (2006.01)
A61B 5/11 (2006.01)
A61B 5/0205 (2006.01)
A61B 5/024 (2006.01)

(52) U.S. Cl.
CPC ........... *G01N 27/028* (2013.01); *A61B 5/053* (2013.01); *A61B 5/742* (2013.01); A61B 5/024 (2013.01); A61B 5/0205 (2013.01); A61B 5/11 (2013.01)

(58) Field of Classification Search
CPC ...... G01N 27/028; A61B 5/053; A61B 5/742; A61B 5/0205; A61B 5/024; A61B 5/11
See application file for complete search history.

(56) References Cited

U.S. PATENT DOCUMENTS

| 8,654,096 | B2* | 2/2014 | Yanase ................. G06F 3/0444 178/18.05 |
| 9,594,103 | B2* | 3/2017 | Kandori ................. G01R 27/26 |
| 10,555,686 | B1* | 2/2020 | Kimoto ................... A61B 5/681 |
| 11,385,194 | B2* | 7/2022 | Yoshida ............ G01N 33/2888 |
| 2013/0102920 | A1* | 4/2013 | Fan ........................ A61B 5/053 600/547 |

* cited by examiner

*Primary Examiner* — Christopher P McAndrew
*Assistant Examiner* — Zannatul Ferdous
(74) *Attorney, Agent, or Firm* — John R. Pessetto; Frank D. Cimino

(57) ABSTRACT

The disclosure provides a measurement circuit. The measurement circuit includes a control engine. An excitation source is coupled to the control engine. A first set of electrodes and a second set of electrodes are coupled to the excitation source and receive current from the excitation source. The control engine operates the excitation source in a first mode and a second mode. The control engine, in the first mode, measures a parasitic impedance associated with the first and the second set of electrodes, and the control engine, in the second mode, measures an impedance of the first and the second set of electrodes and of an external object.

17 Claims, 4 Drawing Sheets

HIGH ACCURACY IMPEDANCE MEASUREMENT

CROSS REFERENCES TO RELATED APPLICATIONS

This application claims priority from India provisional patent application No. 201941026256 filed on Jul. 1, 2019 which is hereby incorporated by reference in its entirety.

TECHNICAL FIELD

The present disclosure is generally related to a biometric monitoring device, and more particularly to a measurement circuit in the biometric monitoring device for accurate measurement of impedance of a biological object.

BACKGROUND

There is a growing interest in measurement of impedance of a biological object including human body because of its use in multiple clinical applications. The impedance of a human body has been extensively used clinically in different areas including nutrition, body composition analysis, nephrology, gastroenterology, obesity analysis and in other critical medical applications. A lot of on-going research is directed towards providing accurate impedance measurement by using methods which are low cost, quick and safe as compared to conventional methods.

The measurement of human body impedance involves attaching electrodes on the skin of the human body. In some systems, four electrodes are attached on different parts of the human body. The electrodes are connected to an impedance measurement instrument. An electric current flows through the electrodes to the human body, and a voltage difference across the electrodes is measured and analyzed by the impedance measurement instrument to generate a value of the impedance of the human body.

The value of human body impedance thus measured is fairly accurate when the impedance of the electrodes is low compared to parasitic impedances associated with the electrodes. However, when the impedance of the electrodes is high and comparable to the parasitic impedances, the value of human body impedance thus measured is inaccurate and the error can be as high as ten times of accurate value. This error is especially visible in wearable biometric monitoring device where the impedance of the contact electrodes is very high and comparable to the parasitic impedances.

SUMMARY

According to an aspect of the disclosure, a measurement circuit is disclosed. The measurement circuit includes a control engine. An excitation source is coupled to the control engine. A first set of electrodes and a second set of electrodes are coupled to the excitation source and receive current from the excitation source. The control engine operates the excitation source in a first mode and a second mode. The control engine, in the first mode, measures a parasitic impedance associated with the first and the second set of electrodes, and the control engine, in the second mode, measures an impedance of the first and the second set of electrodes and of an external object.

BRIEF DESCRIPTION OF THE VIEWS OF DRAWINGS

DETAILED DESCRIPTION OF THE EMBODIMENTS

Figure 1:
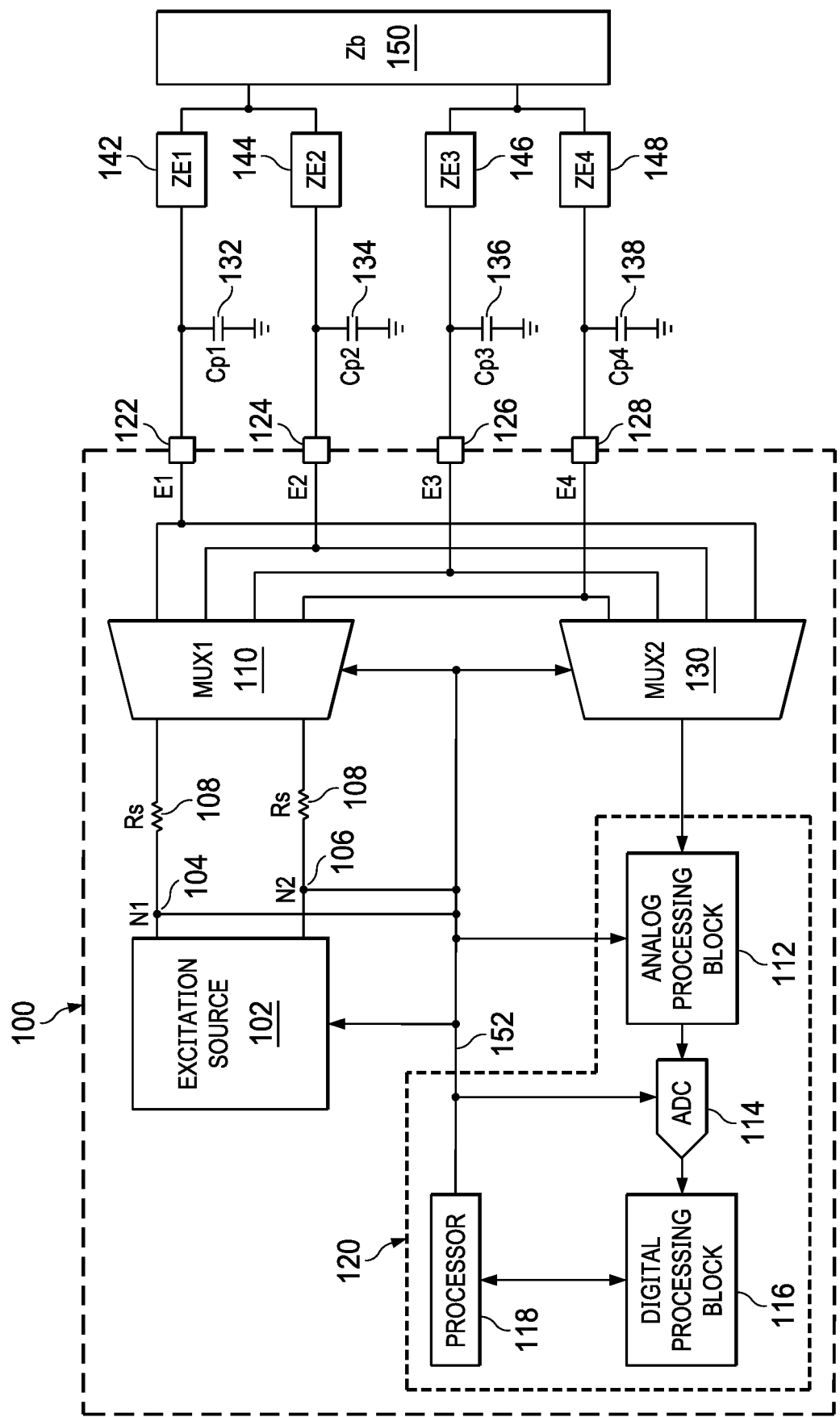
FIG. 1 is a block diagram illustrating a measurement circuit, according to an embodiment.

FIG. 1 is a block diagram illustrating a measurement circuit 100, according to an embodiment. The measurement circuit 100 includes an excitation source 102, a pair of resistors Rs 108, a first multiplexer MUX1 110, and a set of electrodes represented as a first electrode E1 122, a second electrode E2 124, a third electrode E3 126 and a fourth electrode E4 128. The measurement circuit 100 also includes a second multiplexer MUX2 130 and a control engine 120. The first electrode E1 122, the second electrode E2 124, the third electrode E3 126 and the fourth electrode E4 128 are coupled to the first multiplexer MUX1 110 and the second multiplexer MUX2 130.

The control engine 120 includes an analog processing block 112, an analog to digital converter (ADC) 114, a digital processing block 116 and a processor 118. The analog processing block 112 is coupled to the second multiplexer MUX2 130. The ADC 114 is coupled to the analog processing block 112. The digital processing block 116 is coupled between the ADC 114 and the processor 118. The processor 118, the digital processing block 116, the ADC 114, the analog processing block 112, the excitation source 102, the fist multiplexer MUX1 110 and the second multiplexer MUX2 130 are all coupled to each other through a common connection path 152.

A parasitic impedance associated with each electrode of the set of electrodes is represented as a first parasitic impedance Cp1 132, a second parasitic impedance Cp2 134, a third parasitic impedance Cp3 136 and a fourth parasitic impedance Cp4 138. The parasitic impedances are represented as capacitors for purpose of illustration. The parasitic impedances are developed because of routing on the board or PCB where the measurement circuit 100 is placed, and generally it is in the order of Pico farads.

The first parasitic impedance Cp1 132 is associated with the first electrode E1 122, and the second parasitic impedance Cp2 134 is associated with the second electrode E2 124. The third parasitic impedance Cp3 136 is associated with the third electrode E3 126, and the fourth parasitic impedance Cp4 138 is associated with the fourth electrode E4 128.

An impedance of an external object is Zb 150. In one example, the external object is a human body. In another example, the external object is a biological object. In yet another example, the external object is any non-living article. When the external object is coupled to the set of electrodes in the measurement circuit 100, a network is formed between the external object and the measurement circuit 100. This network includes multiple impedances because of the contact made by the electrodes to the external object. ZE1 142 represents an impedance associated with the first electrode E1 122, and ZE2 144 is an impedance associated with the second electrode E2 124. ZE3 146 represents an impedance associated with the third electrode E3 126, and ZE4 148 represents an impedance associated with the fourth electrode E4 128. The measurement circuit 100 may include one or more additional components known to those skilled in the relevant art and are not discussed here for simplicity of the description. The operation of the measurement circuit 100 is now explained in connection with FIG. 2 and FIG. 3.

Figure 2:
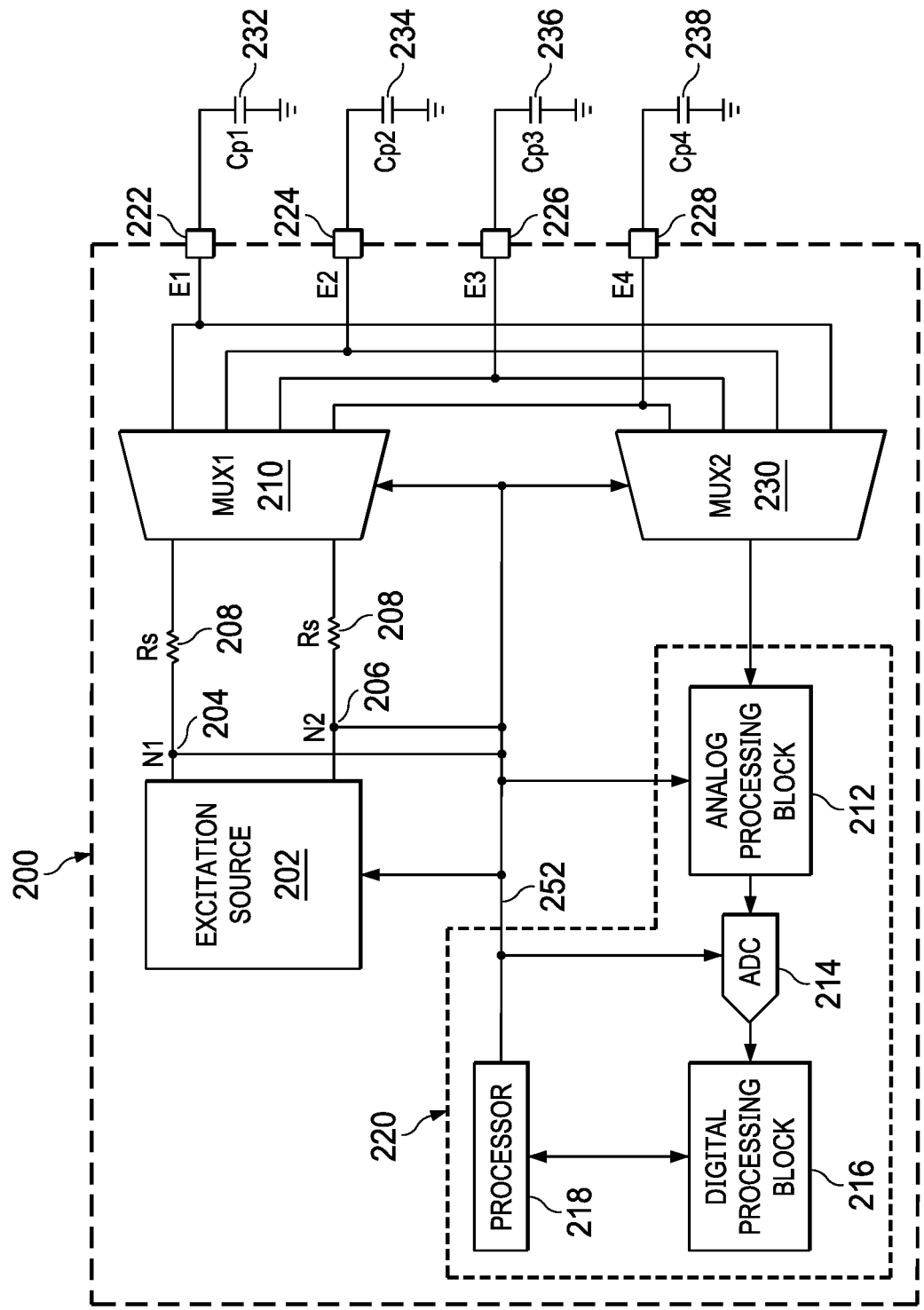
FIG. 2 is a block diagram illustrating a measurement circuit, according to an embodiment.

FIG. 2 is a block diagram illustrating a measurement circuit 200, according to an embodiment. The measurement circuit 200 is similar to the measurement circuit 100, and explains the operation of the measurement circuit 100. In the measurement circuit 100, the control engine 120 operates the excitation source 102 in a first mode and a second mode. The operation in the first mode is explained through FIG. 2 and the operation in the second mode is explained through FIG. 3.

The connections of the measurement circuit 200 are similar to the measurement circuit 100, and are not discussed here for brevity of the description. The measurement circuit 200 is not coupled to an external object. Hence, the impedance of the external object Zb and the impedances (ZE1 to ZE4) developed because of the contact made by the electrodes with the external object are not illustrated in FIG. 2.

The control engine 220 operates an excitation source 202 in the first mode and the second mode. In the first mode, the control engine 220 configures the excitation source 202 to provide current to a first set of electrodes. In one example, the first set of electrodes includes the first electrode E1 222 and the third electrode E3 226. The control engine 220 configures a first multiplexer MUX1 210 such that the current from the excitation source 202 is provided to the first electrode E1 222 and the third electrode E3 226. The excitation source 202 provides current to the first electrode E1 222 and this current traverse back to the excitation source 202 through the third electrode E3 226.

The control engine 220 measures a voltage across the first set of electrodes. The control engine 220 measure voltages at node N1 204 and at node N2 206 which are defined as $V_{N1}$ and $V_{N2}$ respectively. The control engine 220 also measure voltages at the first electrode E1 222 and at the third electrode E3 226 which are defined as $V_{E1}$ and $V_{E3}$. A current through the first parasitic impedance Cp1 232 is measured as:

$$I_{Cp1} = \frac{V_{N1} - V_{E1}}{Rs} \quad (1)$$

The first parasitic impedance Cp1 232 is defined as:

$$Cp1 = \frac{V_{E1}}{I_{Cp1}} \quad (2)$$

A current through the third parasitic impedance Cp3 236 is defined as:

$$I_{Cp3} = \frac{V_{N2} - V_{E3}}{Rs} \quad (3)$$

The third parasitic impedance Cp3 236 is defined as:

$$Cp3 = \frac{V_{E3}}{I_{Cp3}} \quad (4)$$

Thus, using the above steps, the measurement circuit 200 measures the parasitic impedance associated with the first set of electrodes. The first parasitic impedance Cp1 232 is measured by the measurement circuit 200 using equation 2, and the third parasitic impedance Cp3 236 is measured by the measurement circuit 200 using equation 4.

The control engine 220 configures the excitation source 202 to provide current to a second set of electrodes. In one example, the second set of electrodes includes the second electrode E2 224 and the fourth electrode E4 228. The control engine 220 configures the first multiplexer MUX1 210 such that the current from the excitation source 202 is provided to the second electrode E2 224 and the fourth electrode E4 228. The excitation source 202 provides current to the second electrode E2 224 and this current traverse back to the excitation source 202 through the fourth electrode E4 228.

The control engine 220 measures a voltage across the second set of electrodes. The control engine 220 measure voltages at node N1 204 and at node N2 206 which are defined as $V_{N1}$ and $V_{N2}$ respectively. The control engine 220 also measure voltages at the second electrode E2 224 and at the fourth electrode E4 228 which are defined as $V_{E2}$ and $V_{E4}$. A current through the second parasitic impedance Cp2 234 is measured as:

$$I_{Cp2} = \frac{V_{N1} - V_{E2}}{Rs} \quad (5)$$

The second parasitic impedance Cp2 234 is defined as:

$$Cp2 = \frac{V_{E2}}{I_{Cp2}} \quad (6)$$

A current through the fourth parasitic impedance Cp4 238 is defined as:

$$I_{Cp4} = \frac{V_{N2} - V_{E4}}{Rs} \quad (7)$$

The fourth parasitic impedance Cp4 238 is defined as:

$$Cp4 = \frac{V_{E4}}{I_{Cp4}} \quad (8)$$

Thus, using the above steps, the measurement circuit 200 measures the parasitic impedance associated with the second set of electrodes. The second parasitic impedance Cp2 234 is measured by the measurement circuit 200 using equation 6, and the fourth parasitic impedance Cp4 238 is measured by the measurement circuit 200 using equation 8.

In terms of operation of the control engine 120, the processor 118 configures the second multiplexer MUX2 130 to receive voltages measured at the first node N1 104, the second node N2 106 and at each of the first electrode E1 122, the second electrode E2 124, the third electrode E3 126 and the fourth electrode E4 128. Each of these voltages is received by the analog processing block 112 to generate a first signal. The analog to digital converter (ADC) 114 generates a digital signal from the first signal, and the digital processing block 116 generates a second signal from the digital signal. The processor 118 processes the second signal corresponding to each voltage to measure the first parasitic impedance Cp1 232, the third parasitic impedance Cp3 236, the second parasitic impedance Cp2 234 and the fourth parasitic impedance Cp4 238.

Thus, in the first mode, the measurement circuit 200 measures parasitic impedances Cp1 232 to Cp4 238 using voltages measured across the first and the second set of electrodes. It is understood that the combination of electrodes in the first set of electrodes and the second set of electrodes can differ based on the needs of the design. Also, a number of electrodes in the first set of electrodes and the second set of electrodes may vary depending on the application. In addition, the excitation source 202 for the purpose of explanation has been considered as a voltage source. It is understood that the excitation source 202 can also be a current source, in which case the pair of resistors Rs 208 would not be needed and a current through each parasitic impedance is known to the excitation source 202. In this case, the control engine 220 would directly measure the voltage at each electrode.

Figure 3:
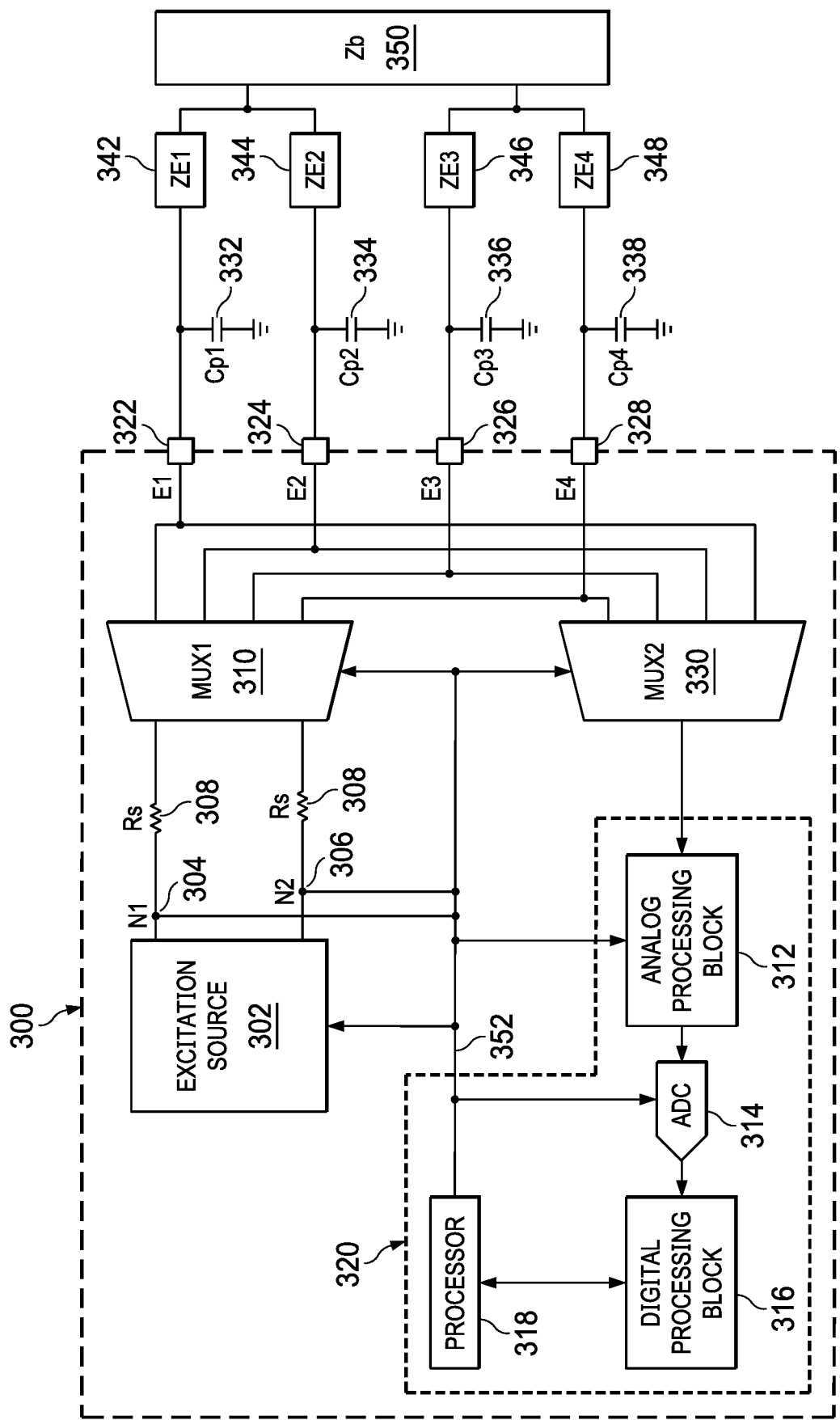
FIG. 3 is a block diagram illustrating a measurement circuit, according to an embodiment.

FIG. 3 is a block diagram illustrating a measurement circuit 300, according to an embodiment. The measurement circuit 300 is similar to the measurement circuit 100, and explains the operation of the measurement circuit 100. In the measurement circuit 100, the control engine 120 operates the excitation source 102 in a first mode and a second mode. The operation in the first mode is explained through FIG. 2 and the operation in the second mode is explained through FIG. 3.

The connections of the measurement circuit 300 are similar to the measurement circuit 100, and are not discussed here for brevity of the description. The measurement circuit 300 is coupled to an external object. Hence, the impedance Zb 350 of the external object and the impedances (ZE1 342 to ZE4 348) developed because of the contact made by the electrodes with the external object are illustrated in FIG. 3.

The control engine 320 operates the excitation source 302 in the first mode and the second mode. In the second mode, the control engine 320 configures the excitation source 302 to provide current to a first set of electrodes. In one example, the first set of electrodes includes the first electrode E1 322 and the third electrode E3 326. A second set of electrodes includes the second electrode E2 324 and the fourth electrode E4 328. The control engine 320 configures the first multiplexer MUX1 310 such that the current from the excitation source 302 is provided to the first electrode E1 322 and the third electrode E3 326. The excitation source 302 provides current to the first electrode E1 322 and this current traverse back to the excitation source 302 through the third electrode E3 326.

The control engine 320 measure voltages at node N1 304 and at node N2 306 which are defined as $V_{N1}$ and $V_{N2}$ respectively. The control engine 320 measure a first set of voltages across each electrode of the first and the second set of electrodes. The first set of voltages are defined as $V_{1E1}$, $V_{1E3}$, $V_{1E2}$ and $V_{1E4}$, where $V_{1E1}$ is a voltage at the first electrode E1 322, $V_{1E3}$ is a voltage at the third electrode E3 326, $V_{1E2}$ is a voltage at the second electrode E2 324 and $V_{1E4}$ is a voltage at the fourth electrode E4 328. A current through the first parasitic impedance Cp1 332 is measured as:

$$I_{1Cp1} = \frac{V_{1E1}}{Cp1} \tag{9}$$

A value of the first parasitic impedance Cp1 332 is obtained from equation 2. A current through the third parasitic impedance Cp3 336 is defined as:

$$I_{1Cp3} = \frac{V_{1E3}}{Cp3} \tag{10}$$

A value of the third parasitic impedance Cp3 336 is obtained from equation 4. A current through the impedance ZE1 342 associated with the first electrode E1 322 is defined as:

$$I_{1ZE1} = \frac{V_{1N1} - V_{1E1}}{Rs} - I_{1Cp1} \tag{11}$$

A current through the impedance ZE3 346 associated with the third electrode E3 326 is defined as:

$$I_{1ZE3} = \frac{V_{1E3} - V_{1N2}}{Rs} + I_{1Cp3} \tag{12}$$

A current through the impedance ZE2 344 associated with the second electrode E2 324 is defined as:

$$I_{1ZE2} = \frac{V_{1E2}}{Cp2} \tag{13}$$

A value of the second parasitic impedance Cp2 334 is obtained from equation 6. A current through the impedance ZE4 348 associated with the fourth electrode E4 328 is defined as:

$$I_{1ZE4} = \frac{V_{1E4}}{Cp4} \tag{14}$$

A value of the fourth parasitic impedance Cp4 338 is obtained from equation 8. The impedance ZE2 344 associated with the second electrode E2 324 is measured as defined below:

$$ZE2 = \frac{(V_{1E1} - I_{1ZE1} \times ZE1) - V_{1E2}}{I_{1ZE2}} \tag{15}$$

Similarly, the impedance ZE3 346 associated with the third electrode E3 326 is measured as defined below:

$$ZE3 = \frac{(V_{1E4} + I_{1ZE4} \times ZE4) - V_{1E3}}{I_{1ZE3}} \tag{16}$$

The control engine 320 configures the excitation source 302 to provide current to the second set of electrodes, which includes the second electrode E2 324 and the fourth electrode E4 328. The control engine 320 configures the first multiplexer MUX1 310 such that the current from the excitation source 302 is provided to the second electrode E2 324 and the fourth electrode E4 328. The excitation source 302 provides current to the second electrode E2 324 and this current traverse back to the excitation source 302 through the fourth electrode E4 328.

The control engine 320 measure voltages at node N1 304 and at node N2 306 which are defined as $V_{N1}$ and $V_{N2}$ respectively. The control engine 320 measure a second set of voltages across each electrode of the first and the second set of electrodes. The second set of voltages are defined as $V_{2E1}$, $V_{2E3}$, $V_{2E2}$ and $V_{2E4}$, where $V_{2E1}$ is a voltage at the first electrode E1 322, $V_{2E3}$ is a voltage at the third electrode E3 326, $V_{2E2}$ is a voltage at the second electrode E2 324 and $V_{2E4}$ is a voltage at the fourth electrode E4 328. A current through the second parasitic impedance Cp2 334 is measured as:

$$I_{2Cp2} = \frac{V_{2E2}}{Cp2} \tag{17}$$

A current through the fourth parasitic impedance Cp4 338 is defined as:

$$I_{2Cp4} = \frac{V_{2E4}}{Cp4} \tag{18}$$

A current through the impedance ZE2 344 associated with the second electrode E2 324 is defined as:

$$I_{2ZE2} = \frac{V_{2N1} - V_{2E2}}{Rs} - I_{2Cp2} \tag{19}$$

A current through the impedance ZE4 348 associated with the fourth electrode E4 328 is defined as:

$$I_{2ZE4} = \frac{V_{2E4} - V_{2N2}}{Rs} + I_{2Cp4} \tag{20}$$

A current through the impedance ZE1 342 associated with the first electrode E1 322 is defined as:

$$I_{2ZE1} = \frac{V_{2E1}}{Cp1} \tag{21}$$

A current through the impedance ZE3 346 associated with the third electrode E3 326 is defined as:

$$I_{2ZE3} = \frac{V_{2E3}}{Cp3} \tag{22}$$

The impedance ZE2 344 associated with the second electrode E2 324 is measured as defined below:

$$ZE2 = \frac{V_{2E2} - (I_{2ZE1} \times ZE1 + V_{2E1})}{I_{2ZE2}} \tag{23}$$

Similarly, the impedance ZE3 346 associated with the third electrode E3 326 is measured as defined below:

$$ZE3 = \frac{(V_{2E4} + I_{2ZE4} \times ZE4) - V_{2E3}}{I_{2ZE3}} \tag{24}$$

The processor 318 in the control engine 320 measures the impedance ZE1 342 associated with the first electrode E1 322 by equating equations 15 and 23, as defined below:

$$ZE1 = \frac{(V_{2E2} - V_{2E1}) \times I_{1ZE2} - (V_{1E1} - V_{1E2}) \times I_{2ZE2}}{I_{1ZE2} \times I_{2ZE1} - I_{1ZE1} \times I_{2ZE2}} \tag{25}$$

The processor 318 in the control engine 320 measures the impedance ZE4 348 associated with the fourth electrode E4 328 by equating equations 16 and 24, as defined below:

$$ZE4 = \frac{(V_{2E4} - V_{2E3}) \times I_{1ZE3} - (V_{1E4} - V_{1E3}) \times I_{2ZE3}}{I_{1ZE4} \times I_{2ZE3} - I_{2ZE4} \times I_{1ZE3}} \tag{26}$$

Using equations 25 and 26, the processor 318 measures the impedance Zb 350 of the external object, as defined below:

$$Zb = \frac{(V_{1E1} - I_{1ZE1} \times ZE1) - (V_{1E3} + I_{1ZE3} \times ZE3)}{I_{1ZE1} - I_{1ZE2}} \tag{27}$$

In terms of operation of the control engine 320, the processor 318 configures the second multiplexer MUX2 330 to receive voltages measured at the first node N1 304, the second node N2 306, the first set of voltages and the second set of voltages. Each of these voltages is sequentially received by the analog processing block 312 to generate a first signal. The analog to digital converter (ADC) 314 generates a digital signal from the first signal, and the digital processing block 316 generates a second signal from the digital signal. The processor 318 processes the second signal corresponding to each voltage to finally measure the impedance Zb 350 of the external object.

Thus, in the first mode, the measurement circuit 300 measures parasitic impedances Cp1 332 to Cp4 338 associated with the electrodes E1 322 to E4 328 respectively. In the second mode, the measurement circuit 300 measures impedances ZE1 342 to ZE4 348 associated with the electrodes E1 322 to E4 328 respectively and the impedance Zb 350 of the external object, using the parasitic impedances measured in the first mode, the first set of voltages and the second set of voltages.

It is understood that the combination of electrodes in the first set of electrodes and the second set of electrodes can differ based on the needs of the design. Also, a number of electrodes in the first set of electrodes and the second set of electrodes may vary depending on the application. In addition, the excitation source 302 for the purpose of explanation has been considered as a voltage source. It is understood that the excitation source 302 can also be a current source, in which case the pair of resistors Rs 308 would not be needed.

The measurement circuit 300 provides accurate measurement of the impedance Zb 350 of the external object even when the parasitic impedance or the impedance associated with each electrode is very high. Also, the measurement circuit 300 provides a mechanism of solving simple linear equations as illustrated in equations 1 to 27 to obtain impedance Zb 350 of the external object. Thus, the complexity of solving non-linear equations is avoided by the measurement circuit 300. The measurement circuit 300 finds application in wearable and medical devices where there is a need for accurate impedance measurement of a human body.

Figure 4:
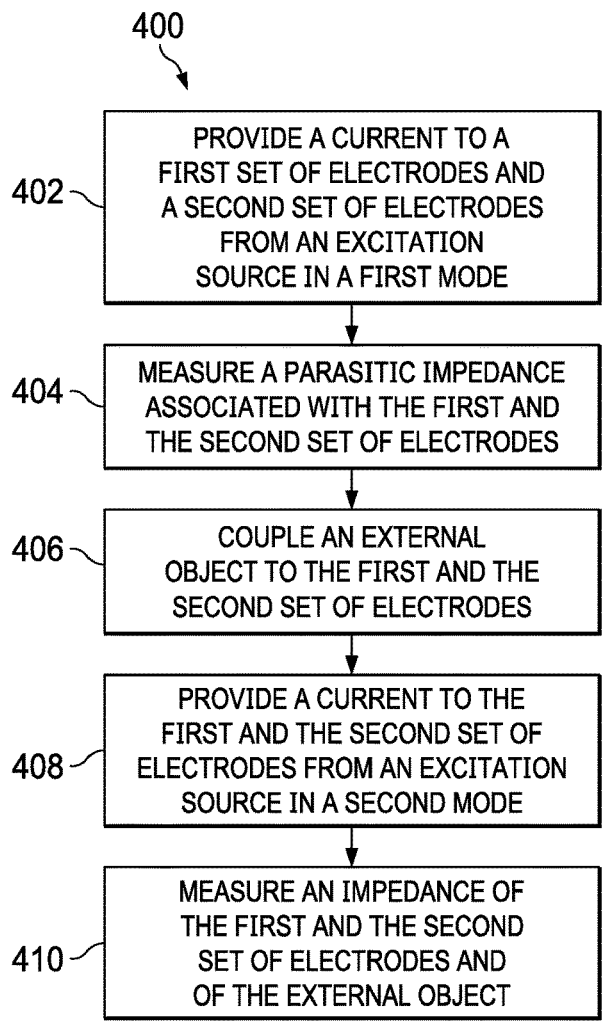
FIG. 4 is a flowchart to illustrate a method of operation of a measurement circuit, according to an embodiment.

FIG. 4 is a flowchart 400 to illustrate a method of operation of a measurement circuit, according to an embodiment. The flowchart 400 is explained in connection with the measurement circuit 100 illustrated in FIG. 1. As discussed, the operation of the measurement circuit 100 is illustrated in connection with FIG. 2 and FIG. 3. As such, measurement circuit 200 and measurement circuit 300 are also used to explain flowchart 400. At step 402, an excitation source provides a current to a first set of electrodes and a second set of electrodes, in a first mode, wherein the external body connection is not present. The parasitic impedance associated with the first and the second set of electrodes is measured at step 404.

In the measurement circuit 200, the control engine 220 configures the excitation source 202 to provide current to a first set of electrodes in the first mode. In one example, the first set of electrodes includes the first electrode E1 222 and the third electrode E3 226. The control engine 220 measure voltages at the first electrode E1 222 and at the third electrode E3 226. The control engine 220 also measure voltages at node N1 204 and at node N2 206. These voltages are used to measure the first parasitic impedance Cp1 232 and the third parasitic impedance Cp3 236.

The control engine 220 configures the excitation source 202 to provide current to a second set of electrodes. In one example, the second set of electrodes includes the second electrode E2 224 and the fourth electrode E4 228. The control engine 220 measures a voltage across the second set of electrodes. The control engine 220 also measure voltages at node N1 204 and at node N2 206. These voltages are used to measure the second parasitic impedance Cp2 234 and the fourth parasitic impedance Cp4 238.

At step 406, an external object is coupled to the first and the second set of electrodes. In FIG. 3, the measurement circuit 300 is coupled to an external object. Hence, the impedance Zb 350 of the external object and the impedances (ZE1 342 to ZE4 348) developed because of the contact made by the electrodes with the external object are illustrated.

At step 408, an excitation source provides a current to the first set of electrodes and the second set of electrodes, in a second mode. An impedance associated with the first and the second set of electrodes and of the external object is measured at step 410. In the second mode, the control engine 320 configures the excitation source 302 to provide current to a first set of electrodes. In one example, the first set of electrodes includes the first electrode E1 322 and the third electrode E3 326. A second set of electrodes includes the second electrode E2 324 and the fourth electrode E4 328. The control engine 320 measure voltages at node N1 304 and at node N2 306. The control engine 320 measure a first set of voltages across each electrode of the first and the second set of electrodes.

The control engine 320 configures the excitation source 302 to provide current to the second set of electrodes, which includes the second electrode E2 324 and the fourth electrode E4 328. The control engine 320 measure voltages at node N1 304 and at node N2 306 which are defined as $V_{N1}$ and $V_{N2}$ respectively. The control engine 320 measure a second set of voltages across each electrode of the first and the second set of electrodes.

The measurement circuit 300 measures impedances ZE1 342 to ZE4 348 associated with the electrodes E1 322 to E4 328 respectively and the impedance Zb 350 of the external object, using the parasitic impedances measured in the first mode, the first set of voltages and the second set of voltages.

In terms of operation of the control engine 320, the processor 318 configures the second multiplexer MUX2 330 to receive voltages measured at the first node N1 304, the second node N2 306, the first set of voltages and the second set of voltages. Each of these voltages is sequentially received by the analog processing block 312 to generate a first signal. The analog to digital converter (ADC) 314 generates a digital signal from the first signal, and the digital processing block 316 generates a second signal from the digital signal. The processor 318 processes the second signal corresponding to each voltage to finally measure the impedance Zb 350 of the external object.

The method illustrated by flowchart 400 provides accurate measurement of the impedance Zb 350 of the external object even when the parasitic impedance or the impedance associated with each electrode is very high. Also, the method provides a mechanism of solving simple linear equations to obtain impedance Zb 350 of the external object. Thus, the complexity of solving non-linear equations is avoided by the method illustrated by flowchart 400. The method finds application in wearable and medical devices where there is a need for accurate impedance measurement of a human body.

Figure 5:
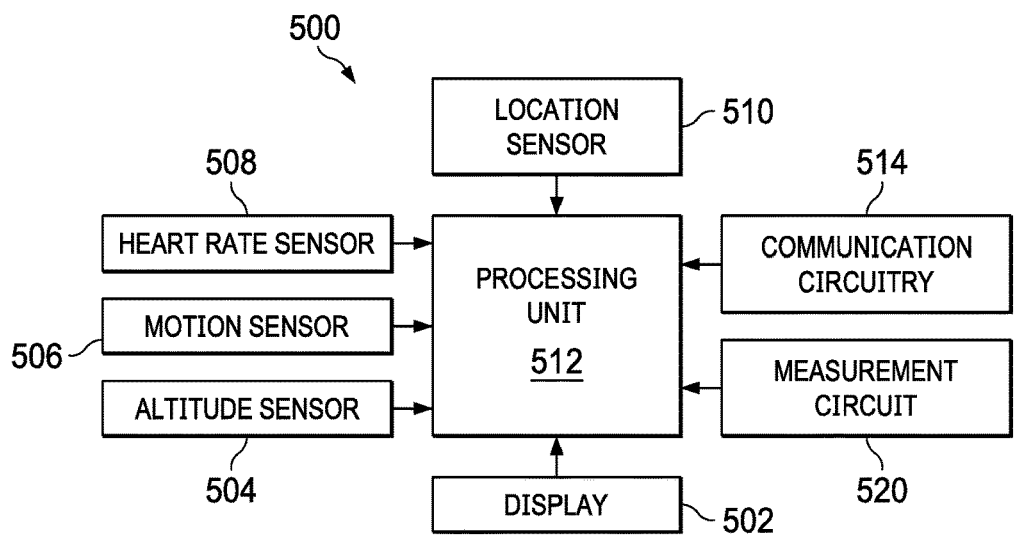
FIG. 5 illustrates a biometric monitoring device, according to an embodiment.

FIG. 5 illustrates a biometric monitoring device 500 according to an embodiment. The biometric monitoring device 500, in one example, is, or is incorporated into, a mobile communication device, such as a mobile phone, a personal digital assistant, a personal computer, or any other type of electronic system. The biometric monitoring device 500, in another example, is a portable personal health monitoring device. The biometric monitoring device 500 can be a wearable device or a non-wearable device. The biometric monitoring device 500 can be installed or part of an electronic or mechanical equipment which is used by human beings. The biometric monitoring device 500 may include one or more additional components known to those skilled in the relevant art and are not discussed here for simplicity of the description.

In some embodiments, the biometric monitoring device 500 comprises a megacell or a system-on-chip (SoC) which includes a processing unit 512 such as a CPU (Central Processing Unit). The processing unit 512 can be, for example, a CISC-type (Complex Instruction Set Computer) CPU, RISC-type CPU (Reduced Instruction Set Computer), or a digital signal processor (DSP). The processing unit 512 is typically, though not necessarily, located on the biometric monitoring device 500.

The biometric monitoring device 500 also includes a variety of sensors including an altitude sensor 504, a motion sensor 506, a heart rate sensor 508, and a location sensor 510. The biometric monitoring device 500 may include one or more types of biometric, physiological and environmental sensors which are not mentioned in FIG. 5 for simplicity of the description.

The biometric monitoring device 500 also includes a communication circuitry 514. In one example, one or more of these sensors are located external to the biometric monitoring device 500. In such cases, the biometric monitoring device 500 may communicate with these external devices using communication circuitry 514 which may be wired or wireless. It is understood that the external device can be a smartphone with one or more sensors and the biometric monitoring device 500 is capable of communicating with such smartphone. All such variations and implementations are understood to be within the scope of this disclosure.

The biometric monitoring device 500 includes a display 502. It is understood, that the display 502 can also be external to the biometric monitoring device 500. The biometric monitoring device 500 may collect one or more types of physiological and/or environmental data from embedded sensors and/or external devices and communicate such data to other devices. The data may be stored, processed, and visualized by the user in a computer, a mobile phone, or a health station.

The biometric monitoring device 500 includes a measurement circuit 520. The measurement circuit 520 is analogous to the measurement circuit 100, in connection and operation. The operation of measurement circuit 520 is similar to the measurement circuit 100 whose operation is explained through FIG. 2 and FIG. 3. The measurement circuit 520, similar to measurement circuit 100, includes a control engine and an excitation source coupled to the control engine. The measurement circuit 520 also includes a first and a second set of electrodes.

The excitation source provides a current to a first set of electrodes and a second set of electrodes, in a first mode. The parasitic impedance associated with the first and the second set of electrodes is measured. In the measurement circuit 520, the control engine configures the excitation source to provide current to a first set of electrodes in the first mode. The control engine measure voltages at the first set of electrode. These voltages are used to measure the parasitic impedance associated with the first set of electrodes.

The control engine configures the excitation source to provide current to a second set of electrodes. The control engine measures a voltage across the second set of electrodes. These voltages are used to measure the parasitic impedance associated with the second set of electrodes.

An external object is coupled to the first and the second set of electrodes in the second mode. The external object, in one example, is a biological object or a human body. In another example, the external object is any non-living article. An excitation source provides a current to the first set of electrodes and the second set of electrodes, in a second mode. The impedance associated with the first and the second set of electrodes and of the external object is measured.

In the second mode, the control engine configures the excitation source to provide current to a first set of electrodes. The control engine measure a first set of voltages across each electrode of the first and the second set of electrodes. The control engine configures the excitation source to provide current to the second set of electrodes. The control engine measure a second set of voltages across each electrode of the first and the second set of electrodes. The measurement circuit 520 measures impedances associated with the electrodes and the impedance of the external object, using the parasitic impedances measured in the first mode, the first set of voltages and the second set of voltages.

The variety of sensors in the biometric monitoring device 500 generates sense signals, and the processing unit 512 generates analytic parameters from the sense signals. The analytic parameters are displayed on the display 502. The processing unit 512 also receives a value of the impedance of the external object from the measurement circuit 520 and displayed on the display 502.

Modifications are possible in the described embodiments, and other embodiments are possible, within the scope of the claims.

What is claimed is:

1. A measurement circuit comprising:
a control engine;
an excitation source coupled to the control engine; and
a first set of electrodes and a second set of electrodes coupled to the excitation source and configured to receive current from the excitation source, wherein the control engine is configured to operate the excitation source in a first mode and a second mode, and wherein, in the second mode:
the control engine configures the excitation source to provide current to the first set of electrodes;
the control engine is configured to measure a first set of voltages across each electrode of the first and the second set of electrodes;
the control engine configures the excitation source to provide current to the second set of electrodes; and
the control engine is configured to measure a second set of voltages across each electrode of the first and the second set of electrodes.

2. The measurement circuit of claim 1, wherein an external object is coupled to the first set of electrodes and the second set of electrodes in the second mode.

3. The measurement circuit of claim 2, wherein in the first mode:
the control engine configures the excitation source to provide current to the first set of electrodes;
the control engine is configured to measure a voltage across each electrode of the first set of electrodes;
the control engine configures the excitation source to provide current to the second set of electrodes; and
the control engine is configured to measure a voltage across each electrode of the second set of electrodes.

4. The measurement circuit of claim 3, wherein the control engine, in the first mode, is configured to measure a parasitic impedance associated with the first and the second set of electrodes by using the voltages measured across the first and the second set of electrodes.

5. The measurement circuit of claim 4, wherein the control engine, in the second mode, is configured to measure an impedance of the first set of electrodes, the second set of electrodes and the external object using the first set of voltages, the second set of voltages and the parasitic impedance.

6. The measurement circuit of claim 1, wherein the control engine further comprises:
an analog processing block coupled to the first and the second set of electrodes;
an analog to digital converter (ADC) coupled to the analog processing block;
a digital processing block coupled to the ADC; and
a processor coupled to the digital processing block.

7. A method comprising:
providing a current to a first set of electrodes and a second set of electrodes from an excitation source in a first mode;
measuring a parasitic impedance associated with the first and the second set of electrodes;
coupling an external object to the first and the second set of electrodes;
providing a current to the first and the second set of electrodes from an excitation source in a second mode; and
measuring an impedance of the first and the second set of electrodes and of the external object, wherein the second mode further includes:

providing current to the first set of electrodes from the excitation source;

measuring a first set of voltages across each electrode of the first and the second set of electrodes;

providing current to the second set of electrodes from the excitation source; and measuring a second set of voltages across each electrode of the first and the second set of electrodes.

8. The method of claim 7, wherein providing current to the first and the second set of electrodes in the first mode further comprises:

providing current to the first set of electrodes from the excitation source;

measuring a voltage across the first set of electrodes;

providing current to the second set of electrodes from the excitation source; and measuring a voltage across the second set of electrodes.

9. The method of claim 8, wherein measuring the parasitic impedance associated with the first and the second set of electrodes further comprises using the voltages measured across the first and the second set of electrodes.

10. The method of claim 9, wherein measuring the impedance of the first and the second set of electrodes and of the external object further comprises using the first set of voltages, the second set of voltages and the parasitic impedance.

11. The method of claim 10, wherein measuring the impedance of the first and the second set of electrodes and of the external object further comprises:

providing sequentially the first and the second set of voltages to an analog processing block to generate a first signal;

generating a digital signal from the first signal by an analog to digital converter (ADC);

generating a second signal from the digital signal by a digital processing block; and processing the second signal generated corresponding to each of the first and the second set of voltages in a processor.

12. A biometric monitoring device comprising:

a plurality of sensors configured to generate sense signals;

a processing unit coupled to the plurality of sensors and configured to generate analytic parameters from the sense signals;

a display coupled to the processing unit and configured to display the analytic parameters generated by the processing unit; and a measurement circuit coupled to the processing unit and the display, the measurement circuit comprising:

a control engine;

an excitation source coupled to the control engine; and a first set of electrodes and a second set of electrodes coupled to the excitation source and configured to receive current from the excitation source, wherein the control engine is configured to operate the excitation source in a first mode and a second mode, and wherein the control engine configures the excitation source to provide current to the first set of electrodes;

the control engine is configured to measure a first set of voltages across each electrode of the first and the second set of electrodes;

the control engine configures the excitation source to provide current to the second set of electrodes; and the control engine is configured to measure a second set of voltages across each electrode of the first and the second set of electrodes.

13. The biometric monitoring device of claim 12, wherein an external object is coupled to the first set of electrodes and the second set of electrodes in the second mode.

14. The biometric monitoring device of claim 13, wherein in the first mode:

the control engine configures the excitation source to provide current to the first set of electrodes;

the control engine is configured to measure a voltage across each electrode of the first set of electrodes;

the control engine configures the excitation source to provide current to the second set of electrodes; and the control engine is configured to measure a voltage across each electrode of the second set of electrodes.

15. The biometric monitoring device of claim 14, wherein the control engine, in the first mode, is configured to measure a parasitic impedance associated with the first and the second set of electrodes by using the voltages measured across the first and the second set of electrodes.

16. The biometric monitoring device of claim 15, wherein the control engine, in the second mode, is configured to measure an impedance of the first set of electrodes, the second set of electrodes and the external object using the first set of voltages, the second set of voltages and the parasitic impedance.

17. The biometric monitoring device of claim 12, wherein the control engine further comprises:

an analog processing block coupled to the first and the second set of electrodes;

an analog to digital converter (ADC) coupled to the analog processing block;

a digital processing block coupled to the ADC; and a processor coupled to the digital processing block.

* * * * *